United States Patent
McDevitt et al.

(10) Patent No.: US 7,655,655 B1
(45) Date of Patent: Feb. 2, 2010

(54) METHOD FOR FACILITATING EXTINCTION TRAINING USING D-CYCLOSERINE

(76) Inventors: Jason P McDevitt, 124 Country Club Dr., Williamsburg, VA (US) 23188; Michael Davis, 5570 Oakwood Dr., Stone Mountain, GA (US) 30087; Kerry J Ressler, 3252 Inman Dr., Atlanta, GA (US) 30319

( * ) Notice: Subject to any disclaimer, the term of this patent is extended or adjusted under 35 U.S.C. 154(b) by 0 days.

(21) Appl. No.: 12/369,761

(22) Filed: Feb. 12, 2009

(51) Int. Cl.
*A61K 31/498* (2006.01)

(52) U.S. Cl. .................................. 514/250; 128/898

(58) Field of Classification Search ............... None
See application file for complete search history.

(56) References Cited

U.S. PATENT DOCUMENTS

2006/0252761 A1* 11/2006 Davis et al. ............... 514/250

OTHER PUBLICATIONS

The University of North Carolina Treatment Programs for Anxiety Disorders (available online at http://psychologyclinic.unc.edu/anxiety/Programs.html) Accessed Jun. 24, 2009.*
The Social Anxiety Institute (available online at www.socialanxietyinstitute.org/ccbtherapy.html) Accessed Jun. 24, 2009.*
The OCD Center of Los Angeles (available online at http://www.ocdla.com/OCDtherapygroups.html) Accessed Jun. 24, 2009.*
Norberg et al., "A Meta-Analysis of D-Cycloserine and the Facilitation of Fear Extinction and Exposure Therapy", Biological Psychiatry, (2008), vol. 63, pp. 1118-1126.

* cited by examiner

*Primary Examiner*—Brandon J Fetterolf
*Assistant Examiner*—Craig Ricci
(74) *Attorney, Agent, or Firm*—Jason P. McDevitt

(57) ABSTRACT

Methods are disclosed for improving treatment of various medical conditions via administration of D-cycloserine to facilitate extinction learning. Specifically, by administering D-cycloserine on a post-extinction training pre-sleep basis, subsequent to extinction training during the day, the methods can improve upon the known ability of D-cycloserine to facilitate extinction learning.

5 Claims, 1 Drawing Sheet

METHOD FOR FACILITATING EXTINCTION TRAINING USING D-CYCLOSERINE

CROSS-REFERENCE TO RELATED APPLICATIONS

Not applicable

STATEMENT REGARDING FEDERALLY SPONSORED RESEARCH OR DEVELOPMENT

Not applicable.

FIELD OF INVENTION

The invention relates generally to the treatment of medical disorders by administering D-cycloserine.

BACKGROUND

D-Cycloserine ("DCS") has long been clinically approved and used as an antibiotic to treat tuberculosis.

Studies in rats showed that DCS could facilitate the psychological process of extinction learning ("extinction"), which led Davis et al. to postulate that DCS could be useful in the treatment of anxiety disorders and other related disorders (see U.S. patent application Ser. No. 10/473,640). Unlike traditional anti-anxiety drugs that are administered on a chronic basis and address physiological symptoms of anxiety, DCS is effective because it facilitates the process of extinction when used on an achronic basis in conjunction with psychotherapy.

Extinction is perhaps most easily explained by referencing the famous studies of Pavlov, who trained dogs to salivate at the sound of a bell by pairing the bell with food. What happens when one continues to ring the bell, but stops bringing the food? Eventually, the dog will stop salivating, and that process is called extinction. The extinction process is often very important in psychotherapy. For example, a returning Iraqi war veteran with post-traumatic stress disorder (PTSD) might feel tremendous stress when driving a car through city streets, a person with acrophobia might feel extreme anxiety when going up in a glass-paneled elevator, and an individual with obsessive-compulsive disorder might feel the need to wash his hands many times after shaking hands with another individual. The goal of psychotherapy for such patients is to extinguish these undesirable responses through an extinction training process, analogous to extinguishing the salivation response in Pavlov's dogs. For example, if an individual with obsessive-compulsive disorder who fears shaking hands with others, based on worries about getting sick, undergoes an extinction training program of shaking hands with many strangers, and does not become sick as a result, then that individual's fear of shaking hands will likely be reduced.

The first human clinical trial demonstrating that DCS could be used in conjunction with extinction training to effectively treat anxiety disorders is described by Davis et al. in U.S. patent application Ser. No. 10/924,591. In this placebo-controlled clinical study, subjects were administered DCS prior to virtual reality therapy sessions for treatment of acrophobia (fear of heights), leading to a significant reduction in the number of therapy sessions required to reach a defined clinical endpoint.

Subsequent human clinical studies, pairing administration of DCS with extinction training for treatment of various anxiety disorders, including social anxiety disorder, panic disorder, and obsessive-compulsive disorder, have further demonstrated that DCS can facilitate the psychological process of extinction and therefore increase the efficacy of extinction training. A meta-analysis covering both animal and human studies has recently been published by Norberg et al. ("A Meta-Analysis of D-Cycloserine and the Facilitation of Fear Extinction and Exposure Therapy", *Biological Psychiatry*, (2008) 63, pp. 1118-1126). In the three-sentence summary of the results in the Abstract section, Norberg et al. state: "D-cycloserine was more effective when administered a limited number of times and when given immediately before or after extinction training/exposure therapy."

In each of the human clinical studies that are described in the meta-analysis, DCS was administered prior to extinction training. DCS is routinely administered to subjects prior to extinction training events such as cognitive behavioral therapy sessions, typically thirty minutes to three hours prior to the extinction training. It also may be administered after extinction training. For example, McDevitt (U.S. patent application Ser. No. 11/347,937) teaches a method wherein DCS is administered to a patient following extinction training only if the extinction training is deemed to have gone well.

It has been proposed that DCS acts by consolidating extinction learning, rather than or in addition to impacting the acquisition of extinction learning. Ledgerwood et al. ("Effects of D-Cycloserine on Extinction of Conditioned Freezing", *Behavioral Neuroscience*, (2003) 117, pp. 341-349) tested this approach in model studies with rats by injecting DCS after extinction training. The results showed that post-extinction training administration of DCS also facilitated extinction learning (as did pre-extinction training administration of DCS), and that the extent of this facilitatory effect decreased as the length of time between extinction training and administration was increased, with no significant facilitatory effect found when the delay between extinction training and administration of DCS was increased to four hours.

Irrespective of whether the main positive impact of DCS on extinction learning derives from improving acquisition or improving consolidation, administering DCS in advance of extinction training has been the preferred approach in the expensive and extensive human clinical trials that have been performed in which DCS is administered on an achronic basis in conjunction with extinction training. DCS has a significant half-life in the body, and by administering DCS prior to extinction training, therapeutically effective levels of DCS can be obtained both during extinction training (during the acquisition of extinction learning phase) and after extinction training (during the consolidation of extinction learning phase).

Accordingly, the current state of the art in using DCS to facilitate extinction training is to administer the drug on an achronic basis sometime prior to extinction training, although there is also evidence that administering DCS immediately after extinction training may also be effective. This practice has been demonstrated to be effective in a number of human clinical trials, and can provide a significant improvement in therapeutic outcomes relative to extinction training alone. However, this practice may not reap all the benefits that administration of DCS can provide, since it neglects the opportunity to take advantage of the fact that certain types of learning are consolidated during sleep. For example, Stickgold and Walker ("Sleep-dependent memory consolidation and reconsolidation", *Sleep Medicine* (2007)8, pp. 331-343) describe numerous types of learning for which the primary consolidation of learning occurs during sleep.

By administering DCS prior to or immediately following, for example, a therapy session during typical working hours, the benefits of DCS upon consolidation of learning are unlikely to be maximized during the portion of the 24-hour cycle (i.e., the sleeping portion) when some of the most effective consolidation of learning takes place. There is a need for improved methods of administering DCS compositions such that DCS can more effectively facilitate consolidation of learning during sleep.

BRIEF SUMMARY OF THE INVENTION

Provided herein is a method for improving treatment of various medical conditions via administration of DCS to facilitate learning. Specifically, by administering DCS within two hours of onset of a subject's night-time sleeping period, subsequent to extinction training during the day, the method can improve upon the well-established ability of DCS to facilitate extinction learning. This night-time administration of DCS may be given in addition to, or in lieu of, the administration of DCS that is typically performed prior to a therapeutically relevant extinction training event such as a psychotherapy session.

Fundamentally, the invention described herein represents an improved method for administering DCS in conjunction with extinction training. By administering DCS within two hours prior to onset of a subject's initial nightly sleep period after the subject undergoes extinction training (i.e., "post-extinction training pre-sleep" administration of DCS), the desired extinction learning can be consolidated to a greater extent than it would be in the absence of post-extinction training pre-sleep DCS administration, thereby resulting in improved therapeutic outcomes.

The invention provides for treating a medical affliction in a subject. The method comprises administering (i) extinction training; and (ii) a therapeutically effective amount of DCS within two hours, within one hour, or within thirty minutes of commencement of the subject's nightly sleep period. Generally, a subject treated according this method would self-administer a therapeutically effective amount of DCS just prior to an attempt to fall asleep for the night.

Suitable medical conditions that can be treated using the methods of the invention include, but are not limited to: an anxiety disorder, a mood disorder, an addictive disorder, an eating disorder, a movement disorder, sexual dysfunction, insomnia, chronic pain, attention-deficit hyperactivity disorder, and an autism spectrum disorder. More broadly, the methods of the invention can be used to augment psychotherapy treatment of any medical afflictions for which extinction training can be beneficial.

For example, the effects of a day-time psychotherapy session on a subject can be facilitated by night-time administration of DCS within two hours of the onset of the subject's initial nightly sleep period subsequent to the psychotherapy session. An initial dose of DCS may be administered prior to the psychotherapy session.

It is believed that chronic administration of DCS is not particularly effective in facilitating the consolidation of extinction learning (Parnas et al., "Effects of Multiple Exposures to d-Cycloserine on Extinction of Conditioned Fear in Rats", *Neurobiol. Learn. Mem.* (2005), 83, pp. 224-231). Consequently, post-extinction training pre-sleep DCS administration, as described herein, is performed on an achronic basis.

For example, provided herein is a method for improving the efficacy of cognitive behavioral therapy comprising achronic administration of DCS to a subject on a post-extinction training pre-sleep basis.

DETAILED DESCRIPTION OF THE INVENTION

Figure 1:
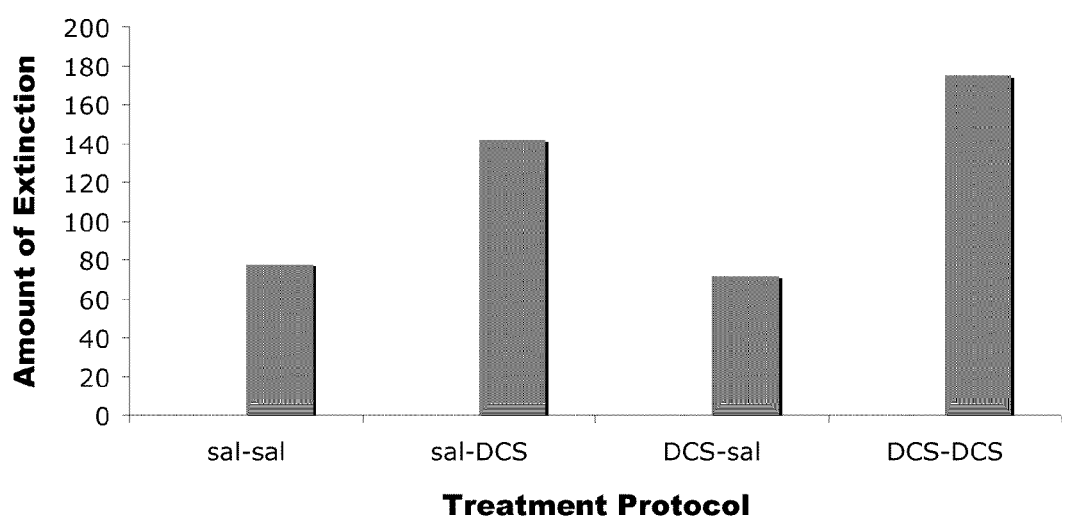
FIG. 1 is a bar graph showing extinction in rats as a function of the drug treatment protocols described in Example 1. More specifically, the graph plots the mean change in percentage fear-potentiated startle for each of four groups of rats administered either DCS or saline prior to extinction training and subsequently administered DCS or saline on a post-extinction training pre-sleep basis (saline/saline, saline/DCS, DCS/saline, and DCS/DCS).

The present invention is directed to the treatment of medical afflictions in a human by administering (i) extinction training; and (ii) DCS, wherein DCS is administered within two hours prior to the person's initial nightly sleep period following extinction training, such that DCS facilitates consolidation of the therapeutically relevant learning derived from the extinction training (i.e., the "extinction learning"), and wherein DCS is administered on an achronic basis.

Described herein are methods for treatment of numerous medical afflictions by achronic, post-extinction training pre-sleep administration of DCS. Such methods can be used to augment therapy (or related treatments) for treatment of, for example, an anxiety disorder, a mood disorder, an addictive disorder, an eating disorder, a movement disorder, sexual dysfunction, insomnia, chronic pain, attention-deficit disorder, an autism spectrum disorder, or other medical conditions for which extinction training is useful. For example, cognitive behavioral therapy has been used to treat schizophrenia, and augmentation of that extinction training with DCS is contemplated according to the methods of the invention when DCS is administered on an achronic, post-extinction training pre-sleep basis.

The methods disclosed herein are used in connection with extinction training, e.g., with psychotherapy. This invention contemplates that upon post-extinction training pre-sleep administration of DCS to a subject, serum levels of DCS in the subject will at certain times during the night be sufficiently high to be therapeutically effective, and these timely serum levels can be achieved using the disclosed methods for administering DCS within two hours of the onset of a subject's nightly sleep period.

As contemplated herein, a subject's nightly sleep period is the portion of the 24-hour daily cycle when the subject sleeps, or intends to sleep, for the longest period. For most individuals, this nightly sleep period takes place during the evening hours. Sleep is the natural state of bodily rest in animals, and includes rapid eye movement (REM) sleep and non-rapid eye movement (NREM) sleep. Human sleep proceeds in cycles of REM and NREM sleep (there are multiple stages of NREM sleep), with a typical full sleep cycle lasting between 90 minutes and 120 minutes. Accordingly, in a nightly sleep period, a subject may complete several sleep cycles. According to the methods of the invention, post-extinction training pre-sleep administration of DCS will typically yield therapeutically effective serum levels of DCS through at least a significant portion of the nightly sleep period, including multiple cycles of REM sleep and NREM sleep.

D-cycloserine, or DCS, refers to the chemical D-cycloserine (CA Index Name: 3-Isoxazolidinone, 4-amino-, (4R)-(9CI); CAS Registry No. 68-41-7), or pharmaceutically acceptable salts thereof. DCS is an FDA (United States Food and Drug Administration)—approved drug for treatment of tuberculosis, and is sold in the United States by Eli Lilly and Company under the trade name Seromycin®. DCS is a structural analog of D-alanine, and is a broad-spectrum antibiotic produced by some strains of Streptomyces orchidaceus and S. garphalus. DCS has antibiotic activity in vitro against growth phase Gram-negative bacteria such as Escherichia coli, some strains of Staphylococcus aureus, and Chlamydia species, among others. The minimum inhibitory concentrations (MIC) in vitro for typical Mycobacterium tuberculosis strains range from about 6-25 µg/mL.

For the treatment of tuberculosis, DCS is generally dosed at 500-1000 mg/day divided twice daily (PDR 1997) with chronic treatment. At a dose of 500 mg/day, serum concentrations of 25-30 µg/ml are generally maintained. Administration of, e.g., known oral capsules of D-cycloserine typically results in peak serum concentrations occurring within 3-8 hours after dosing, with a half-life of 10 hours and primarily renal excretion.

At these typical doses for the treatment of tuberculosis, DCS can give rise to significant neurological side effects in treated subjects. Recorded side effects on chronic dosing schedules (wherein subjects were generally chronically ill with tuberculosis) include drowsiness, depression, headache, confusion, tremor, vertigo, and memory difficulties, paresthesias, and seizure.

As contemplated herein, a therapeutically effective amount of DCS is lower than the amounts typically used for the treatment of tuberculosis. A "therapeutically effective amount" or "therapeutically effective dose" of the pharmacologic agent is an amount of the pharmacologic agent that typically results in an improved treatment, e.g., a greater therapeutic benefit, or a therapeutic benefit for a longer time, relative to that observed in the absence of administering the pharmacologic agent.

In some embodiments, a therapeutically effective amount of DCS used in the disclosed methods relates to a sub-antimicrobial dose of DCS. A sub-antimicrobial dose refers to a dose of DCS that is less than or equal to 2 mg DCS per kg body weight of the subject (i.e., less than or equal to 2 mg/kg), and preferably greater than about 0.2 mg/kg (this lower limit is believed to be needed to maintain efficacy for facilitation of extinction). When administered to a subject, sub-antimicrobial doses of DCS achieve peak serum concentrations in the subject of less than or equal to about 5 µg/mL, although there is substantial variability between subjects. At these low concentrations of DCS, the drug no longer kills most microorganisms, including those that are ordinarily susceptible to higher DCS concentrations typically reached in the body when DCS is used to treat tuberculosis (i.e., based on dosing of 500 mg or 1000 mg per day).

All microorganisms do not have the same susceptibility to DCS. Accordingly, while it is possible that a sub-antimicrobial dose of DCS can still kill a small subset of microorganisms, sub-antimicrobial doses of DCS generally will not have a significant antimicrobial effect in the body. When administered to adult human subjects, a sub-antimicrobial dose of DCS generally comprises a drug formulation (e.g., pill, capsule, tablet) of DCS containing DCS in an amount equal to or less than 100 mg, preferably less than 80 mg DCS (e.g., about 5 mg to about 100 mg, or about 10 mg to about 100 mg, or even about 10 mg to about 80 mg) to provide a greater margin between the concentration of DCS and the minimum inhibitory concentration (MIC) of DCS against microorganisms active in a subject's body.

Children being administered DCS for treatment of tuberculosis are normally dosed at a level between about 10-20 mg/kg. A sub-antimicrobial dose of DCS, when administered to a child subject according to the methods of the present invention, comprises less than or equal to 2 mg/kg, and generally achieves peak serum concentrations of DCS in the child subject of less than or equal to 5 µg/mL.

Because the dosages of DCS contemplated herein are lower than those used to treat tuberculosis, the side effects of DCS will be greatly reduced by post-extinction training pre-sleep administration of DCS, which entails infrequent dosing at levels significantly lower than those routinely used for TB treatment.

When administered to a subject as disclosed herein, a therapeutically effective serum concentration of DCS is achieved within for example 30 minutes, 1 hour, or even 2 hours after administration.

Serum concentration levels of DCS in subjects to whom DCS is administered are a function of numerous factors, including body weight, metabolism, and the amount of drug ingested. The timing of administration and the therapeutically effective dose of DCS in a given subject will depend on the severity of symptoms, in addition to the age, sex, and size of the subject being treated, among other variables. In some embodiments, DCS is administered to a subject prior to or immediately after extinction training, and then again on a post-extinction training pre-sleep basis (i.e., within two hours of the onset of the first nightly sleep period after extinction training).

As a result of concerns about swamping of the NMDA receptor (at which DCS is a partial agonist), or development of tolerance, DCS has typically not been dosed on a chronic, daily basis when it is being used with the intent of augmenting extinction training.

According to the methods of the invention, DCS is administered on an achronic basis. Achronic administration of a pharmacological agent to a subject generally means that the pharmacological agent is not dosed on a daily basis, but rather is used on an intermittent basis. More specifically, it means that the pharmacological agent can be administered to a subject one or more times within a 24-hour period, but then is not administered to the subject again for a period of at least 48 hours. Typically, a pharmacological agent such as DCS that is administered on an achronic basis is not administered to a subject more than two days in a week. According to the methods of the invention, subsequent to post-extinction training pre-sleep DCS administration to a subject, DCS is not administered again to the subject for at least 48 hours, and preferably 72 hours. In many embodiments of the invention, DCS is administered on a once-weekly basis in conjunction with a weekly therapy session. In some cases wherein DCS is administered on an achronic basis according to the methods of the invention, DCS is administered both prior to extinction training (e.g., 30 minutes before psychotherapy) and again subsequent to extinction training on a post-extinction training pre-sleep basis. In such cases, DCS is not administered again to the subject for at least 48 hours following the post-extinction training pre-sleep DCS administration. Alternatively, DCS can be administered immediately following extinction training, and then administered again later that day on a post-extinction training pre-sleep basis.

It is contemplated that other agents may be also administered before, during, or after the administration of extinction training and/or DCS. For example, a B vitamin, such as one or more of the B-complex vitamins, can be administered to a subject in addition to DCS, as part of the contemplated methods. A B-complex vitamin includes thiamine (B1), riboflavin (B2), niacin (B3), pyridoxine (B6), folic acid (B9), cyanocobalamin (B12), pantothenic acid and biotin. For example, pyridoxine can be additionally administered at up to ten times the dosage of DCS. In an embodiment, the DCS for administration as contemplated herein is provided in a composition that includes a B-complex vitamin, e.g., pyridoxine, as a tablet or other composition that includes for example 50 mg DCS and 50 mg pyridoxine. DCS has been reported to reduce the levels of certain important chemicals in the blood of subjects, including calcium, folic acid, magnesium, vitamin K, and vitamin B6 and vitamin B12.

Additionally, achronic, post-extinction training pre-sleep DCS administration to facilitate extinction training in a subject can also be combined with administration of other medications for treatment of the underlying medical condition. For example, many patients with anxiety disorders or mood disorders take pharmacological agents (e.g., selective serotonin reuptake inhibitors such as Xoloft®) on a daily basis, and chronic administration of such pharmacological agents can be combined with achronic post-extinction training pre-sleep DCS administration.

Methods disclosed herein include methods for treating suitable medical conditions in a subject in need thereof comprising: administering extinction training, and subsequently administering a therapeutically effective amount of DCS wherein said DCS is administered on a post-extinction training pre-sleep basis.

Anxiety-related disorders relate to those disorders characterized by fear, anxiety, addiction, and the like. Patients with anxiety-related disorders can have a single such disorder, or can have a constellation of disorders. The anxiety-related disorders contemplated in the present invention include, but are not limited to, anxiety disorders, addictive disorders including substance-abuse disorders, mood disorders (e.g., depression and/or bipolar disorder), movement disorders such as Tourette's syndrome, psychogenic erectile dysfunction (impotence resulting from a man's inability to obtain or maintain an erection of his penis), insomnia (e.g. chronic insomnia), and eating disorders (e.g. anorexia).

Anxiety disorders include, but are not limited to, panic disorder, agoraphobia, social phobia, specific phobia, PTSD, obsessive-compulsive disorder, and generalized anxiety disorder. The disorders contemplated herein are defined in, for example, the DSM-IV (Diagnostic and Statistical Manual of Mental Disorders (4th ed., American Psychiatric Association, Washington D.C., 1994)).

Contemplated methods may be used to treat subjects that experience a deleterious, high-anxiety response to a given stimulus. Such a response is characterized by a high level of anxiety that is disproportionate to the threat represented by the stimulus. Accordingly, a stimulus that generates little if any anxiety in most subjects would generate substantial anxiety in a subject experiencing a deleterious, high-anxiety response. These deleterious, high-anxiety responses cause or exacerbate symptoms characteristic of the medical disorders described herein.

Movement disorders are neurological conditions that affect the speed, fluency, quality, and ease of movement. Representative movement disorders include but are not limited to ataxia, chorea, myoclonus, dystonia, Parkinson's disease, restless leg syndrome, tics, and Tourette's syndrome. Movement disorders typically occur as a result of damage or disease in the basal ganglia region of the brain. Movement disorders can result from age-related changes, medications, genetic disorders, metabolic disorders, disease, stroke, or injury.

Recovery of movement after stroke or injury may be facilitated when treated according to the methods of the invention. More specifically, achronic administration of DCS on a post-extinction training pre-sleep basis can be used after physical therapy to positively impact motor memory consolidation. The motor learning that takes place in these situations is typically consolidated during sleep, and DCS can be administered a post-extinction training pre-sleep basis in an effort to augment this consolidation.

Addictive disorders are disorders characterized by addiction to an activity or substance, and include, for example, alcohol addiction, drug addiction, and gambling addiction.

Depression refers to the clinical condition known as major depressive disorder, and is characterized by a state of intense sadness, melancholia, or despair that has advanced to the point of being disruptive to an individual's social functioning and/or activities of daily living. Depression is alleviated if either (or both) the severity or frequency of a symptom of the depression is reduced. However, a subject can be treated for depression in accordance with the methods of the invention irrespective of whether the treatment actually was successful in alleviating the depression.

Insomnia is defined herein as the inability to fall asleep or to stay asleep for a sufficient amount of time during regular sleeping hours. It includes acute insomnia, which occurs in either a transient or short term form, and chronic insomnia. It also includes initial insomnia, defined as difficulty in falling asleep; middle insomnia, defined as awakening in the middle of the night followed by eventually falling back to sleep, but with difficulty; and terminal insomnia, defined as awakening before one's usual waking time and being unable to return to sleep.

As defined by the National Institute of Mental Health, Autism Spectrum Disorders (ASD), also widely known as Pervasive Developmental Disorders (PDDs), cause severe and pervasive impairment in thinking, feeling, language, and the ability to relate to others. These disorders are usually first diagnosed in early childhood and range from a severe form, called autistic disorder, through pervasive development disorder not otherwise specified (PDD-NOS), to a much milder form, Asperger syndrome. They also include two rare disorders, Rett syndrome and childhood disintegrative disorder.

Attention-Deficit Hyperactivity Disorder (ADHD) is one of the most common mental disorders that develop in children. Children with ADHD typically have impaired functioning in multiple settings, including home, school, and in relationships with peers. Symptoms of ADHD include impulsiveness, hyperactivity, and inattention. Typical treatments include pharmacotherapy and behavioral therapy.

Also contemplated herein are methods for treating pain, e.g., chronic pain (i.e., pain that has lasted more than three months), in a subject in need thereof that includes achronic administration of a therapeutically effective amount of DCS on a post-extinction training pre-sleep basis. Extinction training for subjects experiencing chronic pain can include (but is not limited to), for example, cognitive therapy or biofeedback. Chronic pain in a patient can result in significant psychological and emotional effects and can be severely debilitating.

The goal of extinction training is to pair a stimulus that previously provoked a deleterious, unwanted response with a new learning that will not lead to a negative outcome, thereby generating in a subject a new, more appropriate response to the stimulus to compete with and ideally replace the previous undesirable response. Extinction training frequently exposes a subject to a stimulus or situation in the absence of an aversive consequence, e.g., a subject that has deleterious, high anxiety responses to a given stimulus or situation is exposed to that stimulus or situation in the absence of an aversive consequence. A typical goal of extinction training is to produce new learning in the subject that results from the pairing of the original stimulus or situation with a non-deleterious outcome, thereby generating, in subsequent exposures to the stimulus, a more appropriate response in place of the unwanted response. An extinction learning event refers to a completed stimulus/response extinction training cycle.

One form of extinction training entails psychotherapy. For example, the methods of the invention contemplate treatment of anxiety disorders by: (i) administering psychotherapy to treat an anxiety-related disorder in a suitable human subject, and (ii) administering a therapeutically effective dose DCS to said subject on an achronic, post-training, pre-sleep basis. Suitable methods of psychotherapy include but are not limited to exposure-based psychotherapy, cognitive psychotherapy, and psychodynamically oriented psychotherapy.

One method of psychotherapy that is specifically contemplated is the use of virtual reality (VR) exposure therapy to treat an anxiety disorder using the methods of the invention.

Another method of psychotherapy that is particularly beneficial when utilized in accordance with the methods and compositions of the present invention is cognitive behavioral therapy ("CBT"). CBT is a form of psychotherapy that combines cognitive therapy and behavior therapy, and emphasizes the critical role of thinking in causing people to act and feel as they do. Therefore, if an individual is experiencing unwanted feelings and behaviors, CBT teaches that it is important to identify the thinking that is causing the undesirable feelings and/or behaviors and to learn how to replace this deleterious thinking with thoughts that lead to more desirable reactions. CBT is widely used to help people who are experiencing a range of mental health difficulties, some of which do not conveniently fit definitions of a particular medical affliction. CBT has been used to treat anxiety disorders, mood disorders, addictive disorders, eating disorders, insomnia, chronic pain, schizophrenia, fibromyalgia, ADHD, and autism spectrum disorders, among others. Post-extinction training pre-sleep administration of DCS, subsequent to CBT treatment, can be used to augment the effectiveness of the CBT treatment for these medical conditions.

In one embodiment of the invention, subjects suffering from social anxiety disorder undergo weekly cognitive behavioral therapy sessions to treat the affliction. After each therapy session, subjects are administered a therapeutically effective formulation of DCS (e.g., 50 mg) on a post-extinction training pre-sleep basis. Relative to subjects treated only via cognitive behavioral therapy, or to subjects treated via cognitive behavioral therapy and a placebo, anxiety associated with social anxiety disorder is expected to be reduced to a greater extent in subjects treated with a combination of cognitive behavioral therapy and achronic administration of DCS on a post-extinction training pre-sleep basis. In a variation on this embodiment, the subjects are administered DCS within two hours prior to cognitive behavioral therapy, and then a second dose of DCS is administered on a post-extinction training pre-sleep basis.

In an exemplary clinical trial according to the methods of the invention, subjects suffering from panic disorder undergo weekly cognitive behavioral therapy sessions to treat the affliction. Thirty minutes prior to each therapy session, subjects are administered a capsule containing placebo or DCS. A second capsule containing placebo or DCS is administered subsequent to the therapy session on a post-extinction training pre-sleep basis. Subjects are treated for five weekly sessions, and the four groups (placebo/placebo, placebo/DCS, DCS/placebo, DCS/DCS) of subjects are compared on a number of well-known measures, e.g., panic disorder severity scale. Similar clinical trials can be envisioned for treatment of other afflictions, including but not limited to, for example, depression, alcohol addiction, drug addiction, PTSD, social anxiety disorder, OCD, and simple phobia.

In another embodiment of the invention, DCS is administered after extinction training only if the extinction training yields positive results on that day. For example, a subject undergoing cognitive behavioral therapy for PTSD could be administered DCS on a post-extinction training pre-sleep basis only if the cognitive behavioral therapy was deemed to be successful, as determined by the subject and/or therapist. This method may also be useful when applied to treatment of autism spectrum disorders or attention-deficit hyperactivity disorder.

In another embodiment of the invention, subjects afflicted with anxiety disorders such as PTSD receive extinction training using Eye Movement Desensitization and Reprocessing (EMDR), and subsequently are administered a therapeutically effective dose of DCS on a post-extinction training pre-sleep basis.

Another form of extinction training is provided by biofeedback, which is particularly useful in enabling subjects to learn to control physiological processes that normally occur involuntarily, such as blood pressure, heart rate, muscle tension, and skin temperature. As used herein, "biofeedback" refers to a technique in which subjects are trained to improve their health by using signals from their own bodies to control their own physiological responses.

In one embodiment of the invention, a subject suffering from chronic pain undergoes biofeedback sessions to help alleviate the pain. Upon the conclusion of each session wherein the subject has made progress in learning/developing responses that reduce the chronic pain, the subject is administered DCS (e.g., 75 mg) on a post-extinction training pre-sleep basis in order to consolidate the desired learning.

In another embodiment, a subject suffering from phantom limb syndrome undergoes thermal biofeedback sessions to reduce and hopefully eliminate the symptoms. After each session, the subject is administered a therapeutically effective formulation of DCS on a post-extinction training pre-sleep basis.

In another embodiment, extinction training can be provided by physical therapy, or virtual reality physical therapy such as virtual reality gait therapy. For example, a stroke victim re-learning how to walk can undergo virtual reality gait therapy, and then be administered DCS on an achronic, post-extinction training pre-sleep basis. In one embodiment, virtual reality gait therapy is administered to the subject five or more times per week, and the subject is administered DCS on the two nights wherein the greatest progress was made, i.e., DCS is administered on an achronic, post-extinction training pre-sleep basis.

Another form of extinction training can be provided by pharmacotherapy. For example, a man afflicted with erectile dysfunction can have an extinction learning event based on a positive sexual outcome, including instances wherein the positive sexual outcome was achieved with the pharmacological assistance of a PDE-5 inhibitor such as sildenafil, tadalafil, vardenafil, and/or udenafil. By administering a 50 mg formulation of DCS on a post-extinction training pre-sleep basis to a subject with erectile dysfunction, following a successful sexual outcome wherein the subject utilized sildenafil, the heightened confidence and reduced sexual performance anxiety resulting from a successful outcome can be consolidated in said subject's psyche, thereby facilitating extinction of any deleterious performance anxiety associated with sexual intercourse.

Extinction training does not always require intervention of a trained specialist. Individuals can carry out extinction training on themselves.

Formulations

Pharmaceutical compositions contemplated by the methods of the invention may be formulated and administered to a subject for treatment of various medical conditions as described below.

The invention encompasses the preparation and use of pharmaceutical compositions comprising DCS as an active ingredient useful for treatment of medical afflictions that can be improved by consolidating a desirable response to a particular stimulus, as described above. Such pharmaceutical compositions may consist of DCS alone, in any form suitable for administration to a subject, or the pharmaceutical composition may comprise DCS and one or more pharmaceutically acceptable carriers, one or more additional ingredients, or some combination of these. The active ingredient(s) may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose varies depending upon the subject being treated, and the particular mode of administration. The relative amounts of the active ingredient, the pharmaceutically acceptable carrier, and any additional ingredients in a pharmaceutical composition of the invention may vary, depending upon the identity, size, and condition of the subject treated and further depending upon the route by which the composition is to be administered. By way of example, the composition may comprise between 0.01% and 100% (w/w) active ingredient.

Formulations of the present invention may be administered parenterally as injections (intravenous, intramuscular or subcutaneous), or as drop infusion preparations.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents The terms "parenteral administration" and "administered parenternally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Pharmaceutical compositions that are useful in the methods of the invention may be prepared, packaged, or sold in formulations suitable for oral, rectal, vaginal, intravenous, parenteral, topical, pulmonary, intranasal, buccal, sublingual, ophthalmic, intrathecal or another route of administration.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, as well as condensation products of an alkylene oxide with either: a fatty acid, a long chain aliphatic alcohol, a partial ester derived from a fatty acid and a hexitol, or a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. In one packaging embodiment, a suitable multi-dose unit is a blister-pack having between four and twenty doses of DCS. For example, a 10-pack of DCS capsules may be suitably prescribed to a subject.

EXAMPLES

The example that follows is intended in no way to limit the scope of this invention but instead is provided to illustrate the methods of the present invention. Many other embodiments of this invention will be apparent to one skilled in the art.

Example 1

Effects of Post-Extinction Training Pre-Sleep Administration of DCS on Rats

Subjects. Twenty male, Sprague Dawley rats (300-350 grams) were used. Rats were placed in cages used to measure the acoustic startle reflex (Cassella, J. V., and Davis, M. "The design and calibration of a startle measurement system", *Physiology & Behavior* (1986), 36, pp. 377-383) and, after a 5 minute acclimation period, presented with 50 startle stimuli (50-ms duration, 5-ms rise-decay time), 10 at each of five intensities (95, 100, 105, 110, and 115 dB) in a semi-random order at a 30-s interstimulus interval. The animals were subsequently divided into four groups of five rats, each having similar mean startle amplitudes across the 10 stimuli at the five intensities.

Fear conditioning and testing. On two consecutive training days, animals were placed in the startle chambers and after a 5-min acclimation period, presented with 10 light shock pairings. The shock was presented during the last 500 ms of the 3,700-ms light at an average intertrial interval of 3 minutes (range, 2-4 min). No further shocks were presented thereafter. Twenty-four hours after the second training day, rats were placed in the startle chamber and presented with 30 95-dB startle stimuli (leaders), followed by the first of 10 startle stimuli presented 3.2 seconds after onset of the light that had previously been paired with a shock, and 10 more startle stimuli alone. The two trial types (light-startle and startle-alone) were presented in an irregular balanced order at a 30-s interstimulus interval. Based on the mean difference in startle amplitude between the mean startle amplitude across the last 10 leaders and the mean startle amplitude across the light-startle trials, a percent fear-potentiated startle was computed as: [(mean difference in startle amplitude between the light-startle and leaders)/mean leaders]×100. The rats were divided into four groups.

Extinction training with or without sleep deprivation. One day (24 hrs) later, two groups of rats were injected intraperitoneally with saline and two groups were injected intraperitoneally with 15 mg/kg D-cycloserine (DCS). Fifteen minutes later, extinction training was performed by presenting all rats with 30 presentations of the 3.7-s light in the absence of any shock at a 30-s interstimulus interval). Immediately thereafter, all groups were placed and kept for four hours in plastic containers that were filled with 5 cm of water. The water was used to prevent rats from sleeping after extinction training. They were then taken out of the water, dried off, and injected with either saline or 15 mg/kg DCS, thereby creating four treatment protocol groups with respect to their first and second injection; saline-saline, saline-DCS, DCS-saline, and DCS-DCS. All rats were then placed in clean, dry plastic containers and placed in a quiet, sound-attenuated chamber with the lights on and allowed to sleep. Although sleep was not measured directly, the rats were observed on closed-circuit TV and appeared to sleep (rats tend to sleep in the day, when the lights are on). Thus, rats in the saline-DCS and DCS-DCS groups were given DCS shortly before they fell asleep, enabling an evaluation of the ability of DCS to improve consolidation of extinction during sleep compared with rats given saline prior to sleep (i.e., the saline-saline and DCS-saline groups).

Final test. Two days (48 hrs) later, all rats were given a final test session that consisted of 15 leaders followed by 30 light-startle and 30 startle-alone trials at a 30-s interstimulus interval. Mean percent fear-potentiated startle across the light-startle trials and the last 10 leaders following extinction was computed. For the final analysis, fear-potentiated startle following extinction was subtracted from the percent fear-potentiated startle prior to extinction for each rat. Rats that had less than 50% fear-potentiated startle in the pretest were not used in the analysis, yielding n's of 4 (Sal-Sal), 4 (Sal-DCS), 3 (DCS-Sal) and 3 (DCS-DCS).

Results. Rats administered DCS on a post-extinction training pre-sleep basis (groups Sal-DCS and DCS-DCS) showed the largest decreases in fear-potentiated startle, suggesting that DCS facilitates extinction during sleep. FIG. 1 shows the mean change in percent fear-potentiated startle prior to and after extinction training in the four groups, with values of 93, 164, 78, and 176 for the Sal-Sal, Sal-DCS, DCS-Sal, and DCS-DCS groups, respectively, wherein higher values signify greater extinction. The two groups of rats to which DCS was administered prior to sleep on a post-extinction training pre-sleep basis (in contrast to the groups of rats to which saline was administered prior to sleep) had the largest decreases in fear-potentiated startle, suggesting that giving DCS on a post-extinction training pre-sleep basis enhances consolidation of extinction.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. Contemplated equivalents of the methods of treating anxiety related disorders disclosed here include administering fast acting compositions which otherwise correspond thereto, and which have the same general properties thereof, wherein one or more simple variations of substituents or components are made which do not adversely affect the characteristics of the methods and compositions of interest. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, "an element" means one element or more than one element.

Any ranges cited herein are inclusive, e.g., "between about 25 mg and 75 mg" includes compositions of 25 mg and 75 mg.

We claim:

1. A method for facilitating consolidation of extinction learning to treat an anxiety disorder, comprising administering to a subject in need thereof:
   (a) extinction training; and
   (b) a therapeutically effective amount of D-cycloserine;
      wherein said D-cycloserine is administered at a time that is both greater than four hours after said extinction training and within two hours prior to onset of the subject's initial nightly sleep period subsequent to said extinction training;
      and wherein said D-cycloserine is administered on an achronic basis.

2. The method of claim 1, wherein said extinction training comprises psychotherapy.

3. The method of claim 1, wherein D-cycloserine is administered at a dose between about 25 mg and about 250 mg.

4. The method of claim 1, wherein said D-cycloserine is administered at a dose between about 25 mg and about 75 mg.

5. The method of claim 1, wherein said D-cycloserine is administered at a time that is both subsequent to said extinction training and within thirty minutes prior to the intended onset of a subject's initial nightly sleep period subsequent to said extinction training.

* * * * *